United States Patent [19]

Junino et al.

[11] Patent Number: 5,443,596
[45] Date of Patent: Aug. 22, 1995

[54] KERATINOUS FIBER DYEING COMPOSITIONS AND PROCESSES UTILIZING OXIDATION DYE PRECURSORS IN COMBINATION WITH DIMETHOXY META-AMINOPHENOL COUPLERS

[75] Inventors: Alex Junino, Livry-Gargan; Nicole Bonaventure, Vincennes; Alain Lagrange, Coupvray, all of France

[73] Assignee: L'Oreal, Paris, France

[21] Appl. No.: 167,918

[22] PCT Filed: Jun. 25, 1992

[86] PCT No.: PCT/FR92/00580

§ 371 Date: Dec. 21, 1993

§ 102(e) Date: Dec. 21, 1993

[87] PCT Pub. No.: WO93/00066

PCT Pub. Date: Jul. 1, 1993

[30] Foreign Application Priority Data

Jun. 26, 1991 [FR] France ............... 91 07889

[51] Int. Cl.⁶ .............................................. A61K 7/13
[52] U.S. Cl. .............................................. 8/442; 8/406; 8/408; 8/409; 8/410; 8/411; 8/421
[58] Field of Search ............. 8/405, 406, 408, 410, 8/412, 421, 409, 411; 564/443

[56] References Cited

U.S. PATENT DOCUMENTS

| | | | |
|---|---|---|---|
| 3,834,866 | 9/1974 | Pum | 8/11 |
| 4,008,999 | 2/1977 | Kalopissis et al. | 8/10.2 |
| 4,125,601 | 11/1978 | Bugaut et al. | 8/10.1 |
| 4,152,112 | 5/1979 | Bugaut et al. | 8/10.2 |
| 4,288,622 | 9/1981 | Kalopissis et al. | 8/410 |
| 4,311,478 | 1/1982 | Bugaut et al. | 8/410 |
| 5,180,399 | 1/1993 | Grollier et al. | 8/405 |

FOREIGN PATENT DOCUMENTS

| | | |
|---|---|---|
| 0215560 | 3/1987 | European Pat. Off. . |
| 2262022 | 9/1975 | France . |
| 2348911 | 11/1977 | France . |
| 2364888 | 4/1988 | France . |
| 1949749 | 4/1971 | Germany . |
| 1617885 | 6/1971 | Germany . |
| 2211517 | 7/1989 | United Kingdom . |

OTHER PUBLICATIONS

Bogert et al, "Further Studies of Syringic Acid and its Derivatives", Journal of the American Chemical Society, vol. 51, No. 2, Feb. 1929, pp. 569-576.
Chemical Abstracts, vol. 96, No. 16, Apr. 1982, Abstract No. 133123w re JP-A 81 102 851.
11th Collective Index, 1982-1986 Chemical Substances, pp. 367CS and 16084CS.

Primary Examiner—Paul Lieberman
Assistant Examiner—Caroline L. Dusheck
Attorney, Agent, or Firm—Cushman Darby & Cushman

[57] ABSTRACT

A composition for dyeing keratinous fibers includes, in a suitable dyeing medium, at least one oxidation dye precursor and at least one coupler of formula (I)

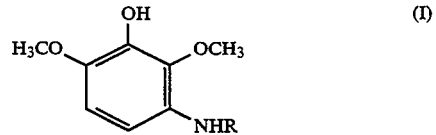

wherein R is hydrogen, $C_1$-$C_4$ lower alkyl, $C_1$-$C_6$ monohydroxyalkyl, $C_2$-$C_6$ polyhydroxyalkyl, or alkylcarbonyl where the alkyl groups have one to four carbon atoms, or the acid addition salts thereof. Also disclosed is a method of dyeing hair using the disclosed composition, certain novel meta-aminophenols and the use of the latter as couplers.

16 Claims, No Drawings

KERATINOUS FIBER DYEING COMPOSITIONS AND PROCESSES UTILIZING OXIDATION DYE PRECURSORS IN COMBINATION WITH DIMETHOXY META-AMINOPHENOL COUPLERS

The present invention relates to new meta-aminophenols, to dyeing compositions for keratinous fibers, and especially for human hair, containing at least one meta-aminophenol as coupler, combined with at least one oxidation dye precursor, as well as to a dyeing process employing said compositions.

It is customary, for the dyeing of keratinous fibers such as human hair or furs, to employ dyeing compositions containing oxidation dye precursors, and especially para-phenylenediamines, ortho-aminophenols or para-aminophenols, which are designated generally by the term oxidation bases.

It is also known that, in order to vary the hues obtained with these oxidation bases, color modifiers or couplers are used, and especially meta-phenylenediamines, meta-aminophenols and meta-diphenols.

In the alkaline oxidizing media normally used in oxidation dyeing, para-phenylenediamines and para-aminophenols give rise, in the presence of couplers such as meta-aminophenols, to colored indophenols or indoanilines.

It is important, moreover, that the oxidation bases and the couplers which are used in oxidation dyeing compositions should impart to the hair colorations which are stable to light, to washing and to inclement weather.

It is also necessary for the compounds used to display a good level of safety.

Many couplers of the type of meta-aminophenols substituted on the aromatic ring are already known. However, a large number of them do not meet the desired requirements.

The Applicants has just discovered new meta-aminophenols which combine a very good level of safety with the dyeing qualities of a good coupler, and which may hence be advantageously used as couplers in combination with oxidation dye precursors, in particular of the para type, in oxidation dyeing compositions for keratinous fibers, in an alkaline or acid medium.

The present invention relates to an oxidation dyeing composition, intended for use for the dyeing of keratinous fibers, and especially human hair, containing, on the one hand at least one para and/or ortho oxidation dye precursor, and on the other hand at least one meta-aminophenol of the formula (I) defined below, as coupler.

Thus, the present invention relates to compositions for the dyeing of keratinous fibers, characterized in that it contains, in a medium suitable for dyeing:
at least one ortho or para type oxidation dye precursor, and
at least one coupler of formula:

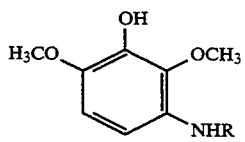
(I)

in which R represents hydrogen, $C_1$–$C_4$ lower alkyl, $C_1$–$C_6$ monohydroxyalkyl; $C_2$–$C_6$ polyhydroxyalkyl; or alkylcarbonyl in which the alkyl groups contain from 1 to 4 carbon atoms;
or their addition salts with an acid.

Among meta-aminophenols of formula (I), the compounds of formula (II):

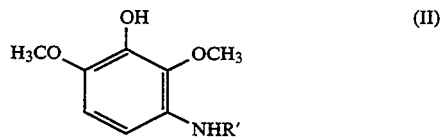
(II)

in which R' represents a $C_1$–$C_4$ alkyl radical or a $C_2$ or $C_3$ mono- or polyhydroxyalkyl radical, as well as their addition salts with an acid, are new and constitute another subject of the invention.

The subject of the invention is also a process dyeing keratinous fibers, employing the compositions according to the invention as well as multi-component dyeing agents which can be in the form of multi-compartment devices or "kits" comprising the different compositions suitable for carrying out the process.

Other subjects of the invention will become apparent on reading the description and the examples which follow.

In the definitions above, among alkyl radicals, methyl, ethyl, propyl, butyl, isopropyl, isobutyl and tert-butyl radicals may be mentioned.

Among monohydroxyalkyl radicals, β-hydroxyethyl, β-hydroxypropyl and γ-hydroxypropyl may be mentioned.

As a polyhydroxyalkyl radical, β, γ-dihydroxypropyl may be mentioned.

The addition salts of the meta-aminophenols with an acid can be, in particular, the addition salts with an inorganic acid such as hydrochloric, hydrobromic or sulfuric acid.

Some compounds of formula (I) are known. The compounds of formula (I) may be prepared from 3-nitro2,6-dimethoxyphenol.

The synthesis of the compound of formula (I) for which R is H may be carried out according to the process described in J.A.C.S., Vol. 51, 1929, page 569.

The synthesis of the compounds of formula (I) for which R is other than H, and of the compounds of formula (II), may be carried out starting from 3-amino-2,6dimethoxyphenol, according to processes based on similar principles and which differ according to the meaning of the radicals R or R'.

Thus, the amine function may be alkylated, hydroxyalkylated or polyhydroxyalkylated according to conventional processes for the alkylation, hydroxyalkylation or polyhydroxyalkylation of aromatic amines.

As an example and according to a first process, for alkylation either dialkyl sulfates or alkyl halides such as methyl iodide or ethyl, isopropyl or butyl bromide may be used, and for hydroxyalkylation or polyhydroxyalkylation hydroxyalkyl or polyhydroxyalkyl halides may be used.

As an example and according to a second process, 3-amino-2,6-dimethoxyphenol may be mesylated. The 3-mesylamino-2,6-dimethoxyphenol obtained is then alkylated, hydroxyalkylated or polyhydroxyalkylated, and then demesylated.

For hydroxyalkylation, the preferred method consists in reacting β-chloroethyl chloroformate with the compound bearing the amine function, and in converting the carbamate obtained to an oxazolidone which is then hydrolyzed to yield the hydroxyethyl derivative. This process is described in French Patent Application No. 2,571,364. The intermediate β-chloroethyl carbamate may also be subjected directly to the action of a strong inorganic base, such as sodium hydroxide or potassium hydroxide, to give the compound (II) in which R' is a β-hydroxyethyl radical.

Among the compounds of formula (I), the following compounds are preferred according to the invention:
3-methylamino-2,6-dimethoxyphenol,
3-ethylamino-2,6-dimethoxyphenol,
3-propylamino-2,6-dimethoxyphenol,
3-butylamino-2,6-dimethoxyphenol,
3-(β-hydroxyethyl)amino-2,6-dimethoxyphenol,
3-acetylamino-2,6-dimethoxyphenol,
3-(β,γ-dihydroxypropyl)amino-2,6-dimethoxyphenol, and
3-amino-2,6-dimethoxyphenol,
or their addition salts with an acid.

Among the especially preferred compounds of formula (I) defined above, some also correspond to the formula (II) and are hence new.

The are
3-methylamino-2,6-dimethoxyphenol,
3-ethylamino-2,6-dimethoxyphenol,
3-propylamino-2,6-dimethoxyphenol,
3-butylamino-2,6-dimethoxyphenol,
3-(β-hydroxyethyl)amino-2,6-dimethoxyphenol,
3-(β,γ-dihydroxypropyl)amino-2,6-dimethoxyphenol,
and their addition salts with an acid.

The oxidation dye precursors used according to the invention are of the ortho and/or para type. They are compounds which are not dyes in themselves, but which form a dye by a process of oxidative condensation, either with themselves or in the presence of a coupler or modifier.

These compounds contain functional groups, either two amino groups or an amino and a hydroxyl group in the para or ortho position with respect to one another.

The para type dye precursors are, in particular, chosen from para-phenylenediamines, para-aminophenols, heterocyclic para precursors such as 2,5-diaminopyridine, 2-hydroxy-5-aminopyridine or tetraaminopyrimidine and bis(phenylene)alkylenediamines also referred to as "double" bases.

As para-phenylenediamines used as oxidation dye precursors according to the invention, there may be mentioned the compounds corresponding to the following formula (III):

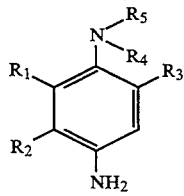

in which:
R$_1$, R$_2$ and R$_3$, which may be identical or different, represent a hydrogen or halogen atom, an alkyl radical having 1 to 4 carbon atoms, an alkoxy radical having 1 to 4 carbon atoms, a carboxyl, sulfo, C$_1$-C$_4$ hydroxyalkyl radical;
R$_4$ and R$_5$, which may be identical or different, represent a hydrogen atom, an alkyl, hydroxyalkyl, alkoxyalkyl, carbamylalkyl, mesylaminoalkyl, acetylaminoalkyl, ureidoalkyl, carbalkoxyaminoalkyl, sulfoalkyl, piperidinoalkyl, morpholinoalkyl radical, a phenyl radical optionally substituted at the para position with an amino group;
these alkyl or alkoxy groups having from 1 to 4 carbon atoms, or alternatively R$_4$ and R$_5$, together with the nitrogen atom to which they are linked, form a piperidino or morpholino heterocycle, with the proviso that R$_1$ or R$_3$ represents a hydrogen atom when R$_4$ and R$_5$ do not represent hydrogen, as well as their salts.

Among these para-phenylenediamines of formula (III), there may be mentioned the following compounds: para-phenylenediamine, p-toluylenediamine, methoxy-para-phenylenediamine, chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, 2-methyl-5-methoxy-para-phenylenediamine, 2,6-dimethyl-5-methoxy-para-phenylenediamine, N,N-dimethyl-para-phenylenediamine, N,N-diethyl-para-phenylenediamine, N,N-dipropyl-para-phenylenediamine, 3-methyl-4-amino-N,N-diethylaniline, N,N-di(β-hydroxyethyl)-para-phenylenediamine, 3-methyl-4-amino-N,N-di (β-hydroxyethyl)aniline, 3-chloro-4-amino-N,N-di (β-hydroxyethyl) aniline, 4-amino-N,N-(ethyl,carbamylmethyl)aniline, 3-methyl-4-amino-N,N-(ethyl,carbamylmethyl)aniline, 4-amino-N,N-(ethyl,β-piperidinoethyl)aniline, 3-methyl-4-amino-N,N-(ethyl, β-piperidinoethyl)aniline, 4-amino-N,N-(ethyl, β-morpholinoethyl)aniline, 3-methyl-4-amino-N,N-(ethyl,β-morpholinoethyl)aniline, 4-amino-N,N-(ethyl, β-acetylaminoethyl)aniline, 4-amino-N-(β-methoxyethyl)aniline, 3-methyl-4-amino-N,N-(ethyl, β-acetylaminoethyl) aniline, 4-amino-N,N-(ethyl,β-mesylaminoethyl)aniline, 3-methyl-4-amino-N,N-(ethyl, (β-mesylaminoethyl)aniline, 4-methyl-4-amino-N,N-(ethyl,β-mesylaminoethyl)aniline, 4-amino-N,N-(ethyl,βsulfoethyl)aniline, 3-methyl-4-amino-N,N-(ethyl,β-sulfoethyl)aniline, N-[(4'-amino)phenyl]morpholine, N-[(4'amino)phenyl]piperidine, 2-hydroxyethyl-para-phenylenediamine, fluoro-para-phenylenediamine, carboxy-para-phenylenediamine, sulfo-para-phenylenediamine, 2-isopropyl-para-phenylenediamine, 2-n-propyl-para-phenylenediamine hydroxymethyl-2-n-propyl-para-phenylenediamine, 2-hydroxymethyl-para-phenylenediamine, N,N-dimethyl-3-methyl-para-phenylenediamine N,N-(ethyl,β-hydroxyethyl)-para-phenylenediamine, N-(dihydroxypropyl)-para-phenylenediamine, N-4'-aminophenyl-para-phenylenediamine and N-phenyl-para-phenylenediamine.

As stated above, these para type oxidation dye precursors may be introduced into the dyeing composition either in free base form, or in the form of salts such as hydrochloride, hydrobromide or sulfate.

The para type dye precursors may also be chosen from p-aminophenols, and when the compounds of formulae (I) and/or (II) are used with p-aminophenols, they give hues which are especially stable to light, to inclement weather and to washing after development in the presence of an oxidizing agent.

Among p-aminophenols, there may be mentioned p-aminophenol, 2-methyl-4-aminophenol, 3-methyl-4-aminophenol, 2-chloro-4-aminophenol, 3-chloro-4-aminophenol, 2,6-dimethyl-4-aminophenol, 3,5-dimethyl-4aminophenol, 2,3-dimethyl-4-aminophenol, 2-hydroxymethyl-4-aminophenol, 2-(β-hydroxyethyl)-4-aminophenol, 2-methoxy-4-aminophenol, 3-methoxy-4-aminophenol, 3-(βhydroxyethoxy)-4-aminophenol, 2-(β-hydroxyethoxy)methyl4aminophenol, 2,5-dimethyl-4-aminophenol, 2-methoxy-methyl-4-aminophenol, 2-ethoxymethyl-4-aminophenol, 2-aminomethyl-4-aminophenol and 2-β-hydroxyethylaminomethyl-4-aminophenol [sic].

As bis(phenylene)alkylenediamine, also referred to as "double" base, there may be mentioned the compounds corresponding to the formula (IV):

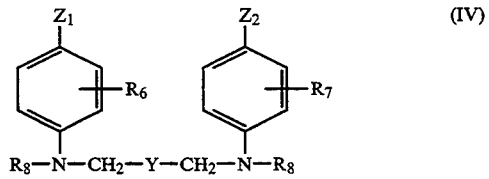

in which:

Z₁ and Z₂, which may be identical or different, represent hydroxyl groups or groups NHR₉, where R₉ denotes a hydrogen atom or a lower alkyl radical;

R₆ and R₇, which may be identical or different, represent either hydrogen atoms or halogen atoms such as bromine, chlorine, fluorine atoms or alternatively alkyl groups;

R₈ represents a hydrogen atom, an alkyl or hydroxyalkyl group or an aminoalkyl group in which the amino residue may be substituted with one or two alkyl groups;

Y represents a radical chosen from the following radicals:

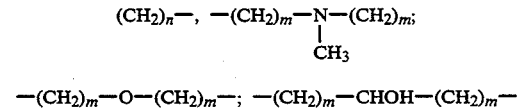

n is an integer between 0 and 8 and m, an integer between 0 and 4, or their addition salts with acids.

In the foregoing definition, the alkyl or alkoxy radicals preferably denote a group having 1 to 4 carbon atoms, and in particular methyl, ethyl, propyl, methoxy, ethoxy.

Among these double bases there may be mentioned compounds chosen from N,N'-bis(β-hydroxyethyl)-N,N'-bis(4'-aminophenyl)-1,3-diamino-2-propanol, N,N'-bis (βhydroxyethyl)-N,N'-bis(4'-aminophenyl)ethylenediamine, N,N'-bis(4-aminophenyl)tetramethylenediamine, N,N'-bis(β-hydroxyethyl)-N,N'-bis(4-aminophenyl)tetramethylenediamine, N,N'-bis(4-methylaminophenyl)tetramethylenediamine, N,N'-bis-(ethyl)-N,N'-bis(4'-amino-3'-methylphenyl)ethylenediamine.

It is also possible, as mentioned above, to use ortho type oxidation dyes combined with the couplers according to the invention. These dyes may be chosen from ortho-aminophenols such as 1-amino-2-hydroxybenzene, 2-amino-5-acetamidophenol, 6-methyl-1-hydroxy-2-aminobenzene or 4-methyl-1-amino-2-hydroxybenzene. ortho-Phenylenediamines may also be used.

In addition to the couplers according to the invention, the dyeing compositions may contain other known couplers. Among these couplers there may be mentioned those chosen from meta-diphenols, meta-aminophenols other than those of formula (I) or (II), meta-phenylenediamines, meta-acylaminophenols, meta-ureidophenols, meta-carbalkoxyaminophenols, α-naphthol, couplers possessing an active methylene group, such as β-keto compounds, pyrazolones, heterocyclic couplers or 4-, 6- or 7-hydroxyindole.

Among these couplers, there may be mentioned, especially, known couplers chosen from 2,4-dihydroxyphenoxyethanol, 2,4-dihydroxyanisole, meta-aminophenol, resorcinol, resorcinol monomethyl ether, 2-methylresorcinol, 2-methyl-5-N-(β-hydroxyethyl)aminophenol, 2-methyl-5-N-(β-mesylaminoethyl)aminophenol, 6-hydroxybenzomorpholine, 2,4-diaminoanisole, 2,4-diaminophenoxyethanol, 6-aminobenzomorpholine, [2-N-(β-hydroxyethyl)-amino-4-amino]phenoxyethanol 2-amino-4-N-(β-hydroxyethyl) aminoanisole, (2,4-diamino)phenyl β,γdihydroxypropyl ether, 2,4-diaminophenoxyethylamine, 1,3-dimethoxy-2,4-diaminobenzene, 2-methyl-5-aminophenol, 2,6-dimethyl-3-aminophenol, 1-amino-3,4-methylenedioxybenzene, 1-hydroxy-3,4-methylenedioxybenzene, 2-chloro-6- methyl-3-aminophenol, 2-methyl-3-aminophenol, 2-chlororesorcinol, 6-methoxy-3-hydroxyethylaminoaniline, 1-ethoxy-2-bis(β-hydroxyethyl)amino-4-aminobenzene, 3-diethylaminophenol, 1,3-dihydroxy-2-methylbenzene, 1-hydroxy-2,4-dichloro-3-aminobenzene, 4,6-hydroxyethoxy1,3-diaminobenzene, 4-methyl-6-ethoxy-1,3-diaminobenzene, 4-chloro-6-methyl-3-aminophenol, 6-chloro-3-trifluoroethylaminophenol, 1,3,5-trimethoxy-2,4-diaminobenzene or their salts.

Direct dyes such as azo, anthraquinone dyes or nitro derivatives of the benzene series may be added to these compositions, as is well known in the state of the art, in particular for the purpose of varying the hue of the colorations provided by the oxidation dye precursors and the coupler of formulae (I) and/or (II), or of enriching these colorations with glints.

The para and/or ortho type oxidation dye precursors as well s the couplers used in the dyeing compositions according to the invention preferably represent collectively from 0.1 to 7% by weight relative to the weight of said composition. The concentration of compounds (I) and/or (II) can vary between 0.05 and 3.5% by weight relative to the total weight of the composition.

The appropriate medium for the dyeing generally consists of an aqueous medium, and its pH can vary between 4 and 12. It is adjusted to the desired value using either an alkalinizing agent such as ammonia solution, alkali metal carbonates, alkanolamines such as mono-, di- or triethanolamine or an acidic agent such as, for example, hydrochloric acid, orthophosphoric acid.

The dyeing compositions according to the invention also contain, in their preferred embodiment, anionic, cationic, nonionic, amphoteric surfactants or mixtures thereof.

Among these surfactants, there may be mentioned alkylbenzenesulfonates, alkylnaphthalenesulfonates, the sulfates, ether sulfates and sulfonates of fatty alcohols, quaternary ammonium salts such as trimethylcetylammonium bromide, cetylpyridinium bromide; optionally oxyethylenated fatty acid ethanolamides; polyoxyethylenated acids, alcohols or amines, polyglycerolated alcohols, polyoxyethylenated or polyglycerolated alkylphenols as well as polyoxyethylenated alkyl sulfates.

These surfactants are present in the compositions according to the invention in proportions of between 0.5 and 40% by weight, and preferably between 4 and 30% by weight, relative to the total weight of the composition.

The medium can also be aqueous-alcoholic. These compositions can thus also contain organic solvents to solubilize compounds which might not be sufficiently soluble in water. Among these solvents, there may be mentioned, as an example, $C_1$-$C_4$ lower alkanols such as ethanol and isopropanol; glycerol; glycols or glycol ethers such as 2-butoxyethanol, ethylene glycol, propylene glycol, diethylene glycol monoethyl ether and monomethyl ether, as well as aromatic alcohols such as benzyl alcohol or phenoxyethanol, and similar products or mixtures thereof.

The solvents are preferably present in proportions of between 1 and 40% by weight, and especially between 5 and 30% by weight, relative to the total weight of the composition.

The thickening agents which may be added to the compositions according to the invention may be chosen from sodium alginate, gum arabic, cellulose derivatives, optionally crosslinked acrylic acid polymers, xanthan gum, scleroglucans. It is also possible to use inorganic thickening agents such as bentonite.

These thickening agents are preferably present in proportions of between 0.1 and 5%, and especially between 0.5 and 3%, by weight relative to the total weight of the composition.

The compositions can contain antioxidants chosen especially from sodium sulfite, thioglycolic acid, sodium bisulfite, dehydroascorbic acid, hydroquinone and homogentisic acid. These antioxidants are present in the composition in proportions of between 0.05 and 1.5% by weight relative to the total weight of the composition.

These compositions may also contain other cosmetically acceptable adjuvants such as, for example, penetrating agents, sequestering agents, perfumes, buffers and the like.

The compositions according to the invention can assume various forms, such as the form of liquids, creams, gels, or any other form suitable for carrying out a dyeing of keratinous fibers, and in particular human hair. These compositions may be packaged in aerosol cans in the presence of a propellent agent.

The dyeing compositions according to the invention, containing a para and/or ortho type oxidation dye precursor and a coupler of formulae (I) and/or (II), are used in the processes for dyeing keratinous fibers, and especially human hair, according to a process that employs development with an oxidizing agent in the form of an oxidizing solution.

The oxidizing solution contains, as oxidizing agent, hydrogen peroxide, urea peroxide, persalts such as ammonium persulfate or alkali metal bromates. It is preferable to use a 20-volumes hydrogen peroxide solution.

The process for dyeing keratinous fibers, and preferably human keratinous fibers, according to the invention, is essentially characterized in that there are applied a component (A) containing, in a medium suitable for dyeing, at least one ortho and/or para type oxidation dye precursor, and a component (B) containing, in a medium suitable for dyeing, at least one coupler of formula (I) or (II), and a component (C) consisting of an oxidizing solution in a sufficient amount to be able to develop a coloration.

The components (A), (B) and (C) may be applied simultaneously or sequentially, the component (A) being applied before the component (B) or mixed with the latter, and the component (B) being applied before the component (C) or mixed with the latter.

According to a first variant, the components (A), (B) and (C) are mixed immediately before application to the hair.

According to a second variant, the mixture of the components (A) and (B) is applied first, followed by the component (C) in a second step.

According to a third variant, the component (A) is applied first, followed by the mixture of the components (B) and (C).

Lastly, according to a fourth variant, the components (A), then (B) and then (C) are applied successively.

The pH of the mixture of the component (C) with the components (A) and (B) or with the component (B), applied to the hair, is between 3.5 and 10.

The process of the invention is carried out by arranging for exposure times, for the different components in the form of mixtures applied in each of the different stages of the process, of between 5 and 45 minutes, and preferably of the order of 10 to 30 minutes.

Thus, according to the first variant, the mixture obtained is applied to the hair and left in place for 5 to 40 minutes, and preferably 10 to 30 minutes, after which the hair is rinsed, washed with shampoo, rinsed again and dried.

The present invention relates to a multi-component dyeing agent for keratinous fibers, especially human hair, characterized in that it contains:
- a component (A) consisting of a composition containing, in a medium suitable for dyeing, an ortho and-/or para type oxidation dye precursor;
- a component (B) consisting of a composition containing, in a medium suitable for dyeing, a compound of formula (I) or (II) as coupler;
- a component (C) consisting of an oxidizing solution, it being possible for one of the components (A) and (B) to be included in the other.

The examples below serve to give a better illustration of the invention without being able to be considered to limit its scope.

PREPARATION EXAMPLES

EXAMPLE 1

Preparation of 3-(β-hydroxyethyl)amino-2,6-dimethoxyphenol

Stage 1: preparation of 3-(chloroethoxycarbonyl)amino-2,6-dimethoxyphenol.

0.1 mol (20.55 g) of 3-amino-2,6-dimethoxyphenol hydrochloride and 11 g of calcium carbonate in 62 ml of dioxane are heated to 90° C.

0.11 mol (11.4 ml) of β-chloroethyl chloroformate is run in dropwise in the course of 15 minutes.

After a further 15 minutes of heating, the reaction medium is filtered in order to remove inorganic salts. On addition of 500 ml of water to the filtrate, the expected product is precipitated. It melts at 79° C. Stage 2: preparation of N-[(3'-hydroxy-2',4'-dimethoxyphenyl)]-1,3-oxazolidin-2-one.

0.079 mol (21.9 g) of 3-(chloroethoxycarbonyl)-amino-2,6-dimethoxyphenol prepared in the preceding step is added to 88 ml of ethanol, and 0.175 mol of 30% sodium methylate in methanol is then run in dropwise. After dilution with water, followed by acidification, the expected product precipitates. It melts at 154° C. Stage 3: preparation of 3-(β-hydroxyethyl)amino-2,6dimethoxyphenol.

0.064 mol (15.3 g) of N-[(3'-hydroxy-2',4'dimethoxyphenyl)]-1,3-oxazolidin-2-one prepared in the preceding step in 45 ml of 5N sodium hydroxide is heated on a boiling water bath. After 30 minutes, the cooled reaction medium is neutralized and the expected product precipitates.

Recrystallized from toluene, it melts at 79° C.

Analysis of the product obtained gives the following results:

| Analysis | Calculated for $C_{10}H_{15}NO_4$ | Found |
|---|---|---|
| C | 56.33 | 56.22 |
| H | 7.09 | 7.04 |
| N | 6.57 | 6.58 |
| O | 30.01 | 29.97 |

EXAMPLE 2

Preparation of 3-methylamino-2,6-dimethoxyphenol hydrochloride

Step 1: preparation of 3-N-tosylamino-2,6-dimethoxy-1tosyloxybenzene.

0.028 mol (5.32 g) of p-toluenesulfonyl chloride is added gradually at a temperature of 40° C. to a solution of 0.01 mol (2.05 g) of 5-amino-2,6-dimethoxyphenol hydrochloride in pyridine.

Stirring is continued at 70° C. for 4 hours after the addition is complete.

The reaction mixture is diluted with ice-cold water and, on acidification with hydrochloric acid, the expected product precipitates.

After draining and washing with water, the product is dried. It melts at 158° C.

Step 2: preparation of 3-N,N-tosyl,methylamino-2,6-dimethoxy-1-tosyloxybenzene.

0.0084 mol (4.0 g) of 3-N-tosylamino-2,6-dimethoxy-1-tosyloxybenzene prepared in the preceding step is dissolved in 12 ml of dimethylformamide. 0.00127 mol (710 mg) of quicklime is added and the temperature is then raised to about 40° C. 0.012 mol (1.1 ml) of methylsulfate is then introduced. When the addition is complete, stirring is maintained for 1 hour.

The expected product precipitates on dilution of the reaction medium with ice-cold water.

After draining, washing with water and acidification with hydrochloric acid, the product is dried. It melts at 124° C.

Step 3: preparation of 3-N,N-tosyl,methylamino-2,6dimethoxyphenol.

0.0081 mol (4.0 g) of the compound prepared in the preceding step (2) is added gradually at a temperature of 90° C. to 80 ml of 7.5N sodium hydroxide. Ethanol is then added until dissolution is complete.

The refluxing temperature is maintained for 15 minutes after the addition is complete.

The reaction medium is diluted with an ice/water mixture. The expected product which has precipitated is drained, washed with water and dried under vacuum in the presence of phosphorus pentoxide. It melts at 110° C.

Step 4: preparation of 3-methylamino-2,6-dimethoxyphenol.

4 ml of hydrochloric acid are added gradually at a temperature of 80° C. to a solution of 2.3 g (0.0068 mol) of the product prepared in the preceding step (3) in 4 ml of acetic acid.

The temperature is maintained at 110° C. for 3 hours after the addition is complete.

The reaction medium is diluted with water, then neutralized with ammonia solution to pH 6.7 and then extracted with ethyl acetate.

The ethyl acetate phases are washed with water, dried over sodium hydroxide and then evaporated to dryness.

On addition of ethanolic hydrogen chloride, 3-methylamino-2,6-dimethoxyphenol hydrochloride is precipitated, which product is recrystallized from isopropanol.

The proton NMR analysis is in agreement with the expected structure.

DYEING EXAMPLE 1

The following dyeing mixture is prepared:

| | |
|---|---|
| 3-Amino-2,6-dimethoxyphenol hydrochloride | 0.514 g |
| p-Phenylenediamine | 0.27 g |
| Polyglycerolated oleic [sic] alcohol containing 2 mol of glycerol | 4.5 g |
| Polyglycerolated oleic [sic] alcohol containing 4 mol of glycerol | 4.5 g |
| Oxyethylenated oleylamine containing 12 mol of ethylene oxide, sold under the name "ETHOMEEN O 12" by the company ARMOON HESS CHEMICAL Ltd | 4.5 g |
| Coconut diethanolamide sold under the name "COMPERLAN KD" by the company HENKEL | 9.0 g |
| Propylene glycol | 4.0 g |
| 2-Butoxyethanol | 8.0 g |
| Ethanol, 96° C. [sic] strength | 6.0 g |
| Diethylenetriaminepentaacetic acid pentasodium salt sold under the name "MASQUOL DTPA" by the company PROTEX | 2.0 g |
| Hydroquinone | 0.15 g |
| Sodium bisulfite solution, 35° Bé | 1.3 g |
| Ammonia solution, 22° Bé | 10.0 g |
| pH = 10 | |
| Water | qs 100.0 g |

At the time of use, 100 g of 20-volumes hydrogen peroxide are added. When applied for 20 minutes at 35° C. to hair which is naturally 90% white, and after shampooing and rinsing, the mixture imparts a slightly red brown coloration thereto.

Degrees Baumé (Bé) are defined in the Merck Index.

DYEING EXAMPLE 2

| | |
|---|---|
| 3-Amino-2,6-dimethoxyphenol hydrochloride | 0.514 g |
| p-Aminophenol | 0.272 g |
| Polyglycerolated oleic [sic] alcohol containing 2 mol of glycerol | 4.5 g |
| Polyglycerolated oleic [sic] alcohol containing 4 mol of glycerol | 4.5 g |
| Oxyethylenated oleylamine containing 12 mol of ethylene oxide, sold under the name "ETHOMEEN O 12" by the company ARMOON HESS CHEMICAL Ltd | 4.5 g |
| Coconut diethanolamide sold under the name "COMPERLAN KD" by the company HENKEL | 9.0 g |
| Propylene glycol | 4.0 g |
| 2-Butoxyethanol | 8.0 g |
| Ethanol, 96° C. [sic] strength | 6.0 g |
| Diethylenetriaminepentaacetic acid pentasodium salt sold under the name "MASQUOL DTPA" by the company PROTEX | 2.0 g |
| Hydroquinone | 0.15 g |
| Sodium bisulfite solution, 35° Bé | 1.3 g |
| Ammonia solution, 22° Bé | 10.0 g |
| pH = 10 | |

| | |
|---|---|
| Water | qs 100.0 g |

At the time of use, 100 g of 20-volumes hydrogen peroxide are added. When applied for 20 minutes at 30° C. to hair which is naturally 90% white, and after shampooing and rinsing, the mixture imparts a light brown coloration thereto.

DYEING EXAMPLE 3

The following dyeing mixture is prepared:

| | |
|---|---|
| 3-Amino-2,6-dimethoxyphenol hydrochloride | 0.61 g |
| p-Phenylenediamine dihydrochloride | 0.627 g |
| Polyglycerolated oleic [sic] alcohol containing 2 mol of glycerol | 4.0 g |
| Polyglycerolated oleic [sic] alcohol containing 4 mol of glycerol, containing 78% of AS | 5.69 g AS |
| Oleic acid | 3.0 g |
| Oleic [sic] amine containing 2 mol of ethylene oxide, sold under the name "ETHOMEEN O 12" by the company AKZO | 7.0 g |
| Diethylaminopropyl laurylaminosuccinamate sodium salt, containing 55% of AS | 3.0 g AS |
| Oleic alcohol | 5.0 g |
| Oleic acid diethanolamide | 12.0 g |
| Propylene glycol | 3.5 g |
| Ethyl alcohol | 7.0 g |
| Dipropylene glycol | 0.5 g |
| Propylene glycol monomethyl ether | 9.0 g |
| Sodium metabisulfite in aqueous solution containing 35% of AS | 0.45 g AS |
| Ammonium acetate | 0.8 g |
| Antioxidant, sequestering agent | qs |
| Perfume, preservatives | qs |
| Monoethanolamine | qs pH 9.8 |
| Demineralized water | qs 100.0 g |

At the time of use, 100 g of 20-volumes hydrogen peroxide, the pH of which is adjusted to between 1 and 1.5 with 85% pure orthophosphoric acid, are added. When applied for 30 minutes to hair which is naturally 90% white, and after shampooing and rinsing, the mixture, the pH of which is approximately 6.5, imparts an iridescent ashen coloration thereto.

DYEING EXAMPLE 4

The following dyeing mixture is prepared:

| | |
|---|---|
| 3-(β-Hydroxyethyl)amino-2,6-dimethoxyphenol | 0.53 g |
| N,N-Di(β-hydroxyethyl)-para-phenylenediamine sulfate hydrate | 0.78 g |
| Polyglycerolated oleic [sic] alcohol containing 2 mol of glycerol | 4.5 g |
| Polyglycerolated oleic [sic] alcohol containing 4 mol of glycerol | 4.5 g |
| Oxyethylenated oleylamine containing 12 mol of ethylene oxide, sold under the name "ETHOMEEN O 12" by the company ARMOON HESS CHEMICAL Ltd | 4.5 g |
| Coconut diethanolamide sold under the name "COMPERLAN KD" by the company HENKEL | 9.0 g |
| Propylene glycol | 4.0 g |
| 2-Butoxyethanol | 8.0 g |
| Ethanol, 96° C. [sic] strength | 6.0 g |
| Diethylenetriaminepentaacetic acid pentasodium salt sold under the name "MASQUOL DTPA" by the company PROTEX | 2.0 g |
| Hydroquinone | 0.15 g |
| Sodium bisulfite solution, 35° Bé | 1.3 g |
| Ammonia solution, 22° Bé | 10.0 g |
| pH = 10.2 | |

| | |
|---|---|
| Water | qs 100.0 g |

At the time of use, 100 g of 20-volumes hydrogen peroxide are added. When applied for 20 minutes at 37° C. to hair which is naturally 90% white, and after shampooing and rinsing, the mixture imparts a slightly red blue-gray coloration thereto.

DYEING EXAMPLE 5

The following dyeing mixture is prepared:

| | |
|---|---|
| 3-Methylamino-2,6-dimethoxyphenol hydrochloride | 0.55 g |
| 2-Methoxymethyl-4-aminophenol | 0.38 g |
| Hydroxyethylcellulose sold under the name "CELLOSIZE WP 03" by the company UNION CARBIDE | 2.0 g |
| Ammonium lauryl sulfate | 5.0 g |
| 2-Butoxyethanol | 15.0 g |
| Ethanol, 96° C. [sic] strength | 6.0 g |
| Ammonia solution, 22° Bé | 10.0 g |
| Sodium bisulfite solution, 35° Bé | 1.5 g |
| Hydroquinone | 0.15 g |
| pH = 10.1 | |
| Water | qs 100.0 g |

At the time of use, 100 g of 20-volumes hydrogen peroxide are added. When applied for 25 minutes at 37° C. on bleached hair, and after shampooing and rinsing, the mixture imparts a green-beige coloration thereto.

DYEING EXAMPLE 6

A dyeing mixture as follows is prepared:

| | |
|---|---|
| 3-(β-Hydroxyethyl)amino-2,6-dimethoxyphenol | 0.53 g |
| 4-Amino-N-(β-methoxyethyl)aniline dihydrochloride | 0.59 g |
| Hydroxyethylcellulose sold under the name "CELLOSIZE WP 03" by the company UNION CARBIDE | 2.0 g |
| Ammonium lauryl sulfate | 5.0 g |
| 2-Butoxyethanol | 15.0 g |
| Ethanol, 96° C. [sic] strength | 5.0 g |
| Diethylenetriaminepentaacetic acid pentasodium salt sold under the name "MASQUOL DTPA" by the company PROTEX | 2.0 g |
| Monoethanolamine | qs pH 9 |
| Water | qs 100.0 g |

At the time of use, 100 g of 20-volumes hydrogen peroxide, the pH of which is adjusted to between 1 and 1.5 with orthophosphoric acid, are added. The final pH is then 6.8.

When applied for 20 minutes at 37° C. to hair which is naturally 90% white, and after shampooing and rinsing, the mixture imparts a light charcoal gray coloration thereto.

DYEING EXAMPLE 7

| | |
|---|---|
| para-Phenylenediamine | 0.07 g |
| 3-(β-Hydroxyethylamino)-2,6-dimethoxyphenol | 0.058 g |
| 3-Amino-6-(β-hydroxyethoxy)aniline dihydrochloride | 0.027 g |
| meta-Aminophenol | 0.05 g |
| Resorcinol | 0.1 g |
| 2-Nitro-6-methyl-3-aminophenol | 0.015 g |
| Cetyl/stearyl alcohol sold under the name | 8.0 g |

-continued

| | |
|---|---|
| "ALFOL 1618" by the company CONDEA Sodium cetyl/stearyl sulfate sold under the name "CIRE DE LANETTE E" by the company HENKEL | 0.5 g |
| Ethoxylated castor oil sold under the name "CEMULSOL B" by the company RHONE POULENC | 1.0 g |
| Oleic diethanolamide | 1.5 g |
| Diethylenetriaminepentaacetic acid pentasodium salt sold under the name "MASQUOL DTPA" by the company PROTEX | 2.5 g |
| Ammonia solution, 22° Bé | 11.0 g |
| Water | qs 100.0 g |
| pH = 10 | |

At the time of use, 100 g of 20-volumes hydrogen peroxide are added. When applied for 25 minutes at 37° C. on hair which is naturally white, and after shampooing and rinsing, the mixture imparts a blueish gray coloration thereto.

DYEING EXAMPLE 8

| | |
|---|---|
| 3-(β-Hydroxyethylamino)-2,6-dimethoxyphenol | 0.3 g |
| 3-Amino-6-methylphenol | 0.7 g |
| 2-Methyl-para-phenylenediamine dihydrochloride | 0.3 g |
| 3-Methyl-4-aminophenol | 0.7 g |
| Oxyethylenated nonylphenol containing 4 mol of ethylene oxide, sold under the name "CEMULSOL NP4" by the company RHONE POULENC | 12.0 g |
| Oxyethylenated nonylphenol containing 9 mol of ethylene oxide, sold under the name "CEMULSOL NP9" by the company RHONE POULENC | 15.0 g |
| Polyglycerolated oleic alcohol containing 2 mol of glycerol | 1.5 g |
| Polyglycerolated oleic alcohol containing 4 mol of glycerol | 1.5 g |
| Propylene glycol | 6.0 g |
| Ethylenediaminetetraacetic acid | 0.12 g |
| Ammonia solution, 22° Bé | 11.0 g |
| Water | qs 100.0 g |
| pH = 9.4 | |

At the time of use, 100 g of 20-volumes hydrogen peroxide are added. When applied for 25 minutes at 37° C. to bleached hair, and after shampooing and rinsing, the mixture imparts a wine-like coloration thereto.

We claim:

1. A composition for dyeing keratinous fibers comprising, in a medium suitable for dyeing said fibers, at least
one oxidation dye precursor selected from the group consisting of a para-aminophenol, a para type heterocyclic precursor, a bis(phenylene)alkylenediamine and a para-phenylenediamine of formula (III):

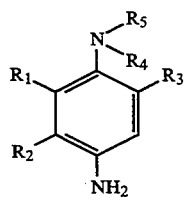

(III)

wherein
$R_1$, $R_2$ and $R_3$, each independently, represent hydrogen, halogen, alkyl having 1–4 carbon atoms, alkoxy having 1–4 carbon atoms, carboxyl, sulfo, or $C_1$–$C_4$ hydroxyalkyl,
$R_4$ and $R_5$, each independently, represent hydrogen, alkyl, hydroxyalkyl, alkoxyalkyl, carbamylalkyl, mesylaminoalkyl, acetylaminoalkyl, ureidoalkyl, carbalkoxyaminoalkyl, sulfoalkyl, piperidinoalkyl, morpholinoalkyl or morpholinoalkoxy wherein the said alkyl or alkoxy groups contain 1 to 4 carbon atoms, phenyl and phenyl substituted at the para position with an amino group, or alternatively, $R_4$ and $R_5$, together with the nitrogen atom to which they are linked, form a piperidino or morpholino heterocycle, with the proviso that $R_1$ or $R_3$ represents hydrogen when $R_4$ and $R_5$ do not represent hydrogen, or a salt thereof,
at least one coupler of formula:

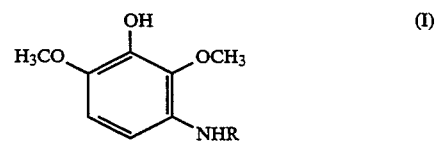

(I)

wherein
R represents hydrogen, $C_1$–$C_4$ alkyl, $C_1$–$C_6$ monohydroxyalkyl, $C_2$–$C_6$ polyhydroxyalkyl, or alkylcarbonyl wherein the alkyl moiety contains from 1–4 carbon atoms,
or an addition salt with an acid.

2. The composition of claim 1 wherein said compounds of formula I are selected from the group consisting of
3-methylamino-2,6-dimethoxyphenol,
3-ethylamino-2,6-dimethoxyphenol,
3-propylamino-2,6-dimethoxyphenol,
3-butylamino-2,6-dimethoxyphenol,
3-(β-hydroxyethyl)amino-2,6-dimethoxyphenol,
3-acetylamino-2,6-dimethoxyphenol,
3-(β,γ-dihydroxypropyl)amino-2,6-dimethoxyphenol and
3-amino-2,6-dimethoxyphenol.

3. The composition of claim 1 wherein said oxidation dye precursor having formula (III) is selected from the group consisting of
p-phenylenediamine,
p-toluylenediamine,
methoxy-para-phenylenediamine,
chloro-para-phenylenediamine,
2,3-dimethyl-para-phenylenediamine,
2,6-dimethyl-para-phenylenediamine,
2,6-diethyl-para-phenylenediamine,
2,5-dimethyl-para-phenylenediamine,
2-methyl-5-methoxy-para-phenylenediamine,
2,6-dimethyl-5-methoxy-para-phenylenediamine,
N,N-dimethyl-para-phenylenediamine,
N,N-diethyl-para-phenylenediamine,
N,N-dipropyl-para-phenylenediamine,
3-methyl-4-amino-N,N-diethylaniline,
N,N-di(β-hydroxyethyl)-para-phenylenediamine,
3-methyl-4-amino-N,N-di(β-hydroxyethyl)aniline,
3-chloro-4-amino-N,N-di(β-hydroxyethyl)aniline,
4-amino-N,N-(ethyl,carbamylmethyl)aniline,
3-methyl-4-amino-N,N-(ethyl,carbamylmethyl)aniline,
4-amino-N,N-(ethyl,β-piperidinoethyl)aniline,
3-methyl-4-amino-N,N-(ethyl,β-piperidinoethyl)aniline, 4-amino-N,N-(ethyl,β-morpholinoethyl)aniline,
3-methyl-4-amino-N,N-(ethyl,β-morpholinoethyl)aniline,
4-amino-N,N-(ethyl,β-acetylaminoethyl)aniline,
4-amino-N-(β-methoxyethyl)aniline,
3-methyl-4-amino-N,N-(ethyl,β-acetylaminoethyl)aniline,
4-amino-N,N-(ethyl,β-mesylaminoethyl)aniline,
3-methyl-4-amino-N,N-(ethyl,β-mesylaminoethyl)aniline,
4-amino-N,N-(ethyl,β-sulfoethyl)aniline,
3-methyl-4-amino-N,N-(ethyl,β-sulfoethyl)aniline,
N-[(4'-amino)phenyl]morpholine,
N-[(4'-amino)phenyl]piperidine,
2-hydroxyethyl-para-phenylenediamine,
fluoro-para-phenylenediamine,
carboxy-para-phenylenediamine,
sulfo-para-phenylenediamine,
2-isopropyl-para-phenylenediamine,
2-n-propyl-para-phenylenediamine,
hydroxy-2-n-propyl-para-phenylenediamine,
2-hydroxymethyl-para-phenylenediamine,
N,N-dimethyl-3-methyl-para-phenylenediamine,
N,N-(ethyl,β-hydroxyethyl)-para-phenylenediamine
N-(dihydroxypropyl-para-phenylenediamine,
N-4'-aminophenyl-para-phenylenediamine,
N-phenyl-para-phenylenediamine.

4. The composition of claim 1 wherein said oxidation dye precursor comprises at least one para-aminophenol selected from the group consisting of:
p-aminophenol,
2-methyl-4-aminophenol,
3-methyl-4-aminophenol,
2-chloro-4-aminophenol,
3-chloro-4-aminophenol,
2,6-dimethyl-4-aminophenol,
3,5-dimethyl-4-aminophenol,
2,3-dimethyl-4-aminophenol,
2-hydroxymethyl-4-aminophenol,
2-(β-hydroxyethyl)-4-aminophenol,
2-methoxy-4-aminophenol,
3-(β-hydroxyethoxy)-4-aminophenol,
2-(β-hydroxyethoxy)methyl-4-aminophenol,
2-ethoxymethyl-4-aminophenol,
3-methoxy-4-aminophenol,
2,5-dimethyl-4-aminophenol,
2-methoxymethyl-4-aminophenol,
2-aminomethyl-4-aminophenol and
2-β-hydroxyethylaminomethyl-4-aminophenol.

5. The composition of claim 1 which contains as said oxidation dye precursor, at least bis(phenylene) alkylenediamine of formula (IV):

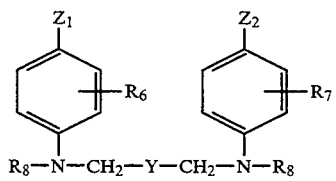  (IV)

wherein
$Z_1$ and $Z_2$, each independently, represent hydroxy or $NHR_9$ wherein $R_9$ represents hydrogen or lower alkyl,
$R_6$ and $R_7$, each independently, represent hydrogen, halogen or alkyl, $R_8$ represents hydrogen, alkyl, hydroxyalkyl, aminoalkyl or aminoalkyl wherein the amino moiety is substituted with one or two alkyl groups,
Y is selected from the group consisting of $-(CH_2)_n-$,

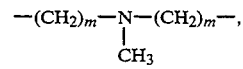

$-(CH_2)_m-O-(CH_2)_m-$ and $-(CH_2)_m-CHOH-(CH_2)_m-$,
n is an integer between 0 and 8 and
m is an integer between 0 and 4, or
the addition salt thereof with an acid.

6. The composition of claim 5 containing at least one bis alkylenediamine selected from the group consisting of:
N,N'-bis(β-hydroxyethyl)-N,N'-bis-(4'-aminophenyl)-1,3-diamino-2-propanol,
N,N'-bis(β-hydroxyethyl)-N,N'-bis(4'-aminophenyl) ethylenediamine,
N,N'-bis(4-aminophenyl) tetramethylenediamine,
N,N'-bis(β-hydroxyethyl)-N,N'-bis(4-aminophenyl) tetramethylenediamine,
N,N'-bis(4-methylaminophenyl) tetramethylenediamine and
N,N'-bis(ethyl)-N,N'-bis(4'-amino-3'-methylphenyl) ethylenediamine.

7. The composition of claim 1 wherein said oxidation dye precursor is an ortho-aminophenol or an ortho-phenylenediamine or an addition salt thereof with an acid.

8. The composition of claim 1 which contains in addition to the coupler of formula (I) another coupler selected from the group consisting of
a meta-diphenol or a meta-aminophenol other than those of formula (I) or (II),
a meta-phenylenediamine,
a meta-acylaminophenol,
a meta-ureidophenol,
a meta-carbalkoxyaminophenol,
α-naphthol,
a coupler possessing an active methylene group,
a pyrazolone heterocyclic coupler and
a 4-, 6- or 7-hydroxyindole.

9. The composition of claim 1 containing at least one coupler selected from the group consisting of
2,4-dihydroxyphenoxyethanol,
2,4-dihydroxyanisole,
metaaminophenol,
resorcinol,
2-methylresorcinol,
resorcinol monomethyl ether,
2-methyl-5-N-(β-hydroxyethyl)aminophenol,
2-methyl-5-N-(β-mesylaminoethyl)aminophenol,
6-hydroxybenzomorpholine,
2,4-diaminoanisole,
2,4-diaminophenoxyethanol,
6-aminobenzomorpholine,
[2-N-(β-hydroxyethyl)amino-4-amino]phenoxyethanol,
2-amino-4-N-(β-hydroxyethyl)aminoanisole,
(2,4-diamino)phenyl-β,γ-dihydroxypropyl ether
2,4-diaminophenoxyethylamine,
1,3-dimethoxy-2,4-diaminobenzene,
2-methyl-5-aminophenol,
2,6-dimethyl-3-aminophenol, 1-amino-3,4-methylenedioxybenzene,
1-hydroxy-3,4-methylenedioxybenzene,
2-chloro-6-methyl-3-aminophenol,
2-methyl-3-aminophenol,
2-chlororesorcinol,
6-methoxy-3-hydroxyethylaminoaniline,
1-ethoxy-2-bis(β-hydroxyethyl)amino-4-aminobenzene,
3-diethylaminophenol,
1,3-dihydroxy-2-methylbenzene,
1-hydroxy-2,4-dichloro-3-aminobenzene,
4,6-hydroxyethoxy-1,3-diaminobenzene,
4-methyl-6-ethoxy-1,3-diaminobenzene,
4-chloro-6-methyl-3-aminophenol,
6-chloro-3-trifluoroethylaminophenol,
2-methyl-5-aminophenol,
1,3,5-trimethoxy-2,4-diaminobenzene
and a salt thereof.

10. The composition of claim 1 wherein said oxidation dye precursor with said coupler represents 0.1 to 7 percent by weight relative to the total weight of said composition.

11. The composition of claim 1 wherein the concentration of said compound of formula (I) ranges from 0.05 to 3.5 percent by weight relative to the total weight of said composition.

12. The composition of claim 1 which also contains a component selected from the group consisting of an alkalinizing agent, a surfactant, an organic solvent, a thickening agent, an antioxidant, a penetrating agent, a sequestering agent, a perfume and a buffer.

13. The composition of claim 1 having a pH ranging from 4 to 12.

14. A process for dyeing keratinous fibers comprising applying to said keratinous fibers a component (A) containing, in a medium suitable for dyeing said keratinous fibers, at least one oxidation dye precursor selected from the group consisting of a para-aminophenol, a para type heterocyclic percursor, a bis(phenylene)alkylenediamine and a paraphenylenediamine of formula (III):

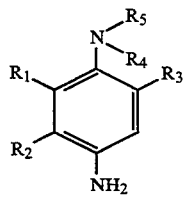

wherein
$R_1$, $R_2$ and $R_3$, each independently, represent hydrogen, halogen, alkyl having 1–4 carbon atoms, alkoxy having 1–4 carbon atoms, carboxyl, sulfo, or $C_1$–$C_4$ hydroxyalkyl,
$R_4$ and $R_5$, each independently, represent hydrogen, alkyl, hydroxyalkyl, alkoxyalkyl, carbamylalkyl, mesylaminoalkyl, acetylaminoalkyl, ureidoalkyl, carbalkoxyaminoalkyl, sulfoalkyl, piperidinoalkyl, morpholinoalkyl or morpholinoalkoxy wherein the said alkyl or alkoxy groups contain 1 to 4 carbon atoms, phenyl and phenyl substituted at the para position with an amino group, or alternatively, $R_4$ and $R_5$, together with the nitrogen atom to which they are linked, form a piperidino or morpholino heterocycle, with the proviso that $R_1$ or $R_3$ represents hydrogen when $R_4$ and $R_5$ do not represent hydrogen, or a salt thereof, in an amount effective for dyeing said keratinous fibers and a component (B) containing, in a medium suitable for dyeing keratinous fibers, at least one coupler of formula (I):

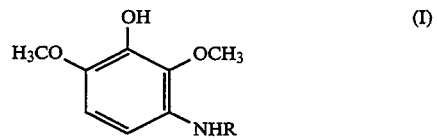

wherein
R represents hydrogen, $C_1$–$C_4$ lower alkyl, $C_1$–$C_6$ monohydroxyalkyl, $C_2$–$C_6$ polyhydroxyalkyl or alkylcarbonyl wherein the alkyl group contains from 1 to 4 carbon atoms, or an acid addition salt thereof, in an amount effective for dyeing said keratinous fibers; and a component (C) comprising an oxidizing solution in an amount sufficient to develop a coloration on said keratinous fibers, said components (A), (B) and (C) being applied simultaneously or sequentially, said component (A) being applied prior to said component (B) or mixed with said component (C), and said component (B) being applied prior to said component (C) or mixed with said component (C).

15. The process of claim 14 wherein the pH of the mixture of said component (C) with said components (A) and (B), or with said component (B) is between 3.5 and 10.

16. A multi-component dyeing agent for keratinous fibers comprising
a component (A) comprising a composition comprising in a medium suitable for dyeing said keratinous fibers at least one oxidation dye precursor selected from the group consisting of a para-aminophenol, a para type heterocyclic precursor, a bis (phenylene) alkylenediamine and a para-phenylenediamine of formula (III)

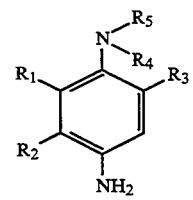

wherein
$R_1$, $R_2$ and $R_3$, each independently, represent hydrogen, halogen, alkyl having 1–4 carbon atoms, alkoxy having 1–4 carbon atoms, carboxyl, sulfo, or $C_1$–$C_4$ hydroxyalkyl,
$R_4$ and $R_5$, each independently, represent hydrogen, alkyl, hydroxyalkyl, alkoxyalkyl, carbamylalkyl, mesylaminoalkyl, acetylaminoalkyl, ureidoalkyl, carbalkoxyaminoalkyl, sulfoalkyl, piperidinoalkyl, morpholinoalkyl or morpholino alkoxy wherein the alkyl or alkoxy groups contain 1 to 4 carbon atoms, phenyl and phenyl substituted at the para position with an amino group, or alternatively, $R_4$ and $R_5$ together with the nitrogen atoms to which they are linked, form a piperidino or morpholino heterocycle, with the proviso that $R_1$ or $R_3$ represents hydrogen when R₄ and R₅ do not represent hydrogen, or a salt thereof, and component (B) comprising a composition containing in a medium suitable for dyeing said keratinous fibers a compound of formula (I):

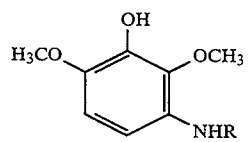

wherein
R represents hydrogen, $C_1$–$C_4$ lower alkyl, $C_1$–$C_6$-monohydroxyalkyl; $C_2$–$C_6$ polyhydroxyalkyl or alkylcarbonyl wherein the alkyl group contains form 1 to 4 carbon atoms, or an acid addition salt thereof, as a coupler in an amount effective to dye said keratinous fibers, and
a component (C) comprising an oxidizing solution, with the proviso that one of components (A) and (B) can be included in the other.

* * * * *